(12) United States Patent
Heide et al.

(10) Patent No.: US 11,364,375 B2
(45) Date of Patent: Jun. 21, 2022

(54) MEDICAL TREATMENT DEVICE AND HOSE SET FOR A MEDICAL TREATMENT DEVICE AND METHOD FOR MONITORING A PERISTALTIC HOSE PUMP

(71) Applicant: FRESENIUS MEDICAL CARE DEUTSCHLAND GMBH, Bad Homburg (DE)

(72) Inventors: Alexander Heide, Eppstein (DE); Arne Peters, Bad Homburg (DE); Dejan Nikolic, Bad Schwalbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 676 days.

(21) Appl. No.: 16/098,137

(22) PCT Filed: May 4, 2017

(86) PCT No.: PCT/EP2017/060721
§ 371 (c)(1),
(2) Date: Nov. 1, 2018

(87) PCT Pub. No.: WO2017/191292
PCT Pub. Date: Nov. 9, 2017

(65) Prior Publication Data
US 2019/0143015 A1 May 16, 2019

(30) Foreign Application Priority Data
May 6, 2016 (DE) .................. 10 2016 005 467.0

(51) Int. Cl.
*A61M 60/857* (2021.01)
*F04B 43/12* (2006.01)
(Continued)

(52) U.S. Cl.
CPC ............ *A61M 60/857* (2021.01); *A61M 1/14* (2013.01); *A61M 1/367* (2013.01);
(Continued)

(58) Field of Classification Search
CPC . A61M 60/857; A61M 1/367; F04B 43/1253; F04B 51/00
See application file for complete search history.

(56) References Cited

U.S. PATENT DOCUMENTS

| 4,411,651 A | 10/1983 | Schulman |
| 4,778,636 A | 10/1988 | Krieg et al. |

(Continued)

FOREIGN PATENT DOCUMENTS

| EP | 0542140 A2 | 5/1993 |
| EP | 0745400 A2 | 12/1996 |

(Continued)

OTHER PUBLICATIONS

International Preliminary Report on Patentability issued in corresponding International Patent Application No. PCT/EP2017/060721 dated Nov. 6, 2018 (7 pages).

(Continued)

*Primary Examiner* — Ariana Zimbouski
(74) *Attorney, Agent, or Firm* — Kilyk & Bowersox, P.L.L.C.

(57) ABSTRACT

The invention relates to a medical treatment apparatus comprising a tube set 20, a peristaltic pump 6 for conveying fluid, and a monitoring apparatus 15 for monitoring the occlusion of the positive displacement elements 13A, 13B of the peristaltic pump. In addition, the invention relates to a tube set 20 for a medical treatment apparatus, and to a method for monitoring the occlusion of the occlusion elements of a peristaltic pump for conveying a fluid for a medical treatment apparatus. The invention is based on the (Continued)

fact that the occlusion of the positive displacement elements 13A, 13B of the peristaltic pump 6 is monitored in order to monitor the fluid flow in the hose line 5. For this purpose, the electrical resistance or a variable which correlates with the electrical resistance is measured between a first and a second electrode 16A, 16B, the first electrode 16A being arranged on the hose line 5 upstream of the occlusion elements 12 of the peristaltic pump 6 and the second electrode 16b being arranged on the hose line downstream of the occlusion elements such that an electrical contact is produced between the first and second electrode 16A, 16B and the fluid flowing in the hose line 5. The electrodes 16A, 16B are preferably integral component parts of a connecting piece 10, by means of which the hose segment 5A to be inserted into the peristaltic pump 6 is fixed in the form of a loop.

15 Claims, 4 Drawing Sheets

(51) Int. Cl.
| | | |
|---|---|---|
| *F04B 51/00* | (2006.01) | |
| *F04B 43/00* | (2006.01) | |
| *F04B 49/06* | (2006.01) | |
| *A61M 60/50* | (2021.01) | |
| *A61M 60/279* | (2021.01) | |
| *A61M 1/14* | (2006.01) | |
| *A61M 1/36* | (2006.01) | |
| *G01N 27/10* | (2006.01) | |

(52) U.S. Cl.
CPC .......... *A61M 60/279* (2021.01); *A61M 60/50* (2021.01); *F04B 43/0081* (2013.01); *F04B 43/12* (2013.01); *F04B 43/1253* (2013.01); *F04B 49/06* (2013.01); *F04B 51/00* (2013.01); *G01N 27/10* (2013.01); *A61M 2205/3317* (2013.01); *F04B 2205/07* (2013.01); *F04B 2205/09* (2013.01)

(56) References Cited

U.S. PATENT DOCUMENTS

| | | | |
|---|---|---|---|
| 2007/0286756 A1 | 12/2007 | Jones et al. | |
| 2009/0053083 A1 | 2/2009 | Kopperschmidt | |
| 2013/0056419 A1 | 3/2013 | Curtis | |
| 2014/0010675 A1* | 1/2014 | Kent | F04B 43/1238 417/53 |
| 2014/0037480 A1* | 2/2014 | Fini | A61M 60/268 417/477.1 |

FOREIGN PATENT DOCUMENTS

| | | |
|---|---|---|
| JP | 2014518525 A | 7/2014 |
| WO | 2005111424 A1 | 11/2005 |
| WO | 2007104435 A2 | 9/2007 |
| WO | 2012110313 A1 | 8/2012 |
| WO | 2012143432 A | 10/2012 |

OTHER PUBLICATIONS

International Search Report issued in corresponding International Patent Application No. PCT/EP2017/060721 (with English translation) dated Jul. 7, 2017 (9 pages).

EPO Official Communication pursuant to Article 94(3) EPC received in corresponding European U.S. Appl. No. 17721,389.9 dated Oct. 30, 2019 (5 pages).

Notice of Reasons for Refusal issued by the Japan Patent Office for corresponding Japanese Patent Application No. 2018-558191, dated Mar. 23, 2021 (seven pages), in English.

* cited by examiner

MEDICAL TREATMENT DEVICE AND HOSE SET FOR A MEDICAL TREATMENT DEVICE AND METHOD FOR MONITORING A PERISTALTIC HOSE PUMP

This application is a National Stage Application of PCT/EP2017/060721, filed May 4, 2017, which claims priority to German Patent Application No. 10 2016 005 467.0, filed May 6, 2016.

The invention relates to a medical treatment apparatus, in particular an extracorporeal blood treatment apparatus, comprising a tube set, a peristaltic pump for conveying fluid and a monitoring apparatus for monitoring the occlusion of the positive displacement elements of the peristaltic pump. In addition, the invention relates to a tube set for a medical treatment apparatus, in particular an extracorporeal blood treatment apparatus, and to a method for monitoring the occlusion of the occlusion elements of a peristaltic pump for conveying a fluid for a medical treatment apparatus.

In extracorporeal blood treatment, the blood to be treated flows through the blood chamber of a dialyser in an extracorporeal blood circuit, which dialyser is divided into the blood chamber and a dialysate chamber by a semi-permeable membrane, while dialysate flows through the dialysate chamber of the dialyser in a dialysate system. The extracorporeal blood circuit comprises an arterial hose line, which leads to the blood chamber, and a venous hose line, which leads from the blood chamber. The hose lines of the extracorporeal blood treatment apparatus are generally provided as a tube set intended for single use (disposable). The known blood treatment apparatuses have a blood pump, which is generally arranged upstream of the blood chamber of the dialyser in order to ensure sufficient blood flow in the extracorporeal blood circuit.

The blood pumps have to meet stringent technical requirements. Therefore, only certain types of pump are considered. In practice, hose pumps which convey the patient's blood through the arterial and venous hose lines have proven to be suitable.

The hose pumps are also referred to as peristaltic pumps in accordance with their mode of operation. Their pumping action is based on at least one constriction or closure point (occlusion) moving along the resilient hose line which acts as the pump chamber and, as a result, the enclosed fluid moving in the conveying direction. In the most conventional design of the peristaltic pumps, the resilient hose is completely closed at the moved constriction points. These pumps are therefore also described as occlusive peristaltic pumps.

The movable constriction or closure points, which transport the blood in the pump hose, can be designed in different ways. Roller pumps are known in which the hose is inserted between a stator, which forms a curved roller conveyor a brace, and a rotor, which is rotatably mounted therein and is fitted with rollers, such that the rollers roll on the hose in the conveying direction and exert a contact pressure on the hose. In addition, finger pumps are also known, in which the closure body is formed by a row of movable rods (fingers) arranged along the hose.

An overview of the different designs of roller pumps and finger pumps is given in Dialysetechnik [dialysis technology], 4th edition, Gesellschaft für angewandte Medizintechnik m.b.H and Co. KG, Friedrichsdorf, 1988.

When used in medico-technical devices, in particular blood treatment apparatuses, correct operation of peristaltic pumps has to meet stringent requirements. Peristaltic pumps are used in the known blood treatment apparatuses not only for conveying blood, but also for conveying other fluids, for example dialysate.

During operation of the peristaltic pump, there is the risk of an interruption of the fluid flow in the hose line downstream of the peristaltic pump, for example owing to kinking of the hose line. If the peristaltic pump is operated when the hose line is blocked, there is the risk of the hose line bursting. Since the occlusion elements of known peristaltic pumps are resiliently mounted, said elements can be removed when a predetermined overpressure is exceeded in the hose line, and therefore the pressure in the hose line can be reduced by return flow of the fluid. However, the occlusion of the peristaltic pump is thus removed and therefore correct operation is not ensured. In particular in blood pumps, permanent operation of the pumps when the occlusion elements are removed can cause damage to the blood in the hose segment (haemolysis), which makes prompt detection of the blockage desirable.

The blockage of a hose line during operation of a peristaltic pump cannot be reliably detected only by monitoring the pressure in the hose line, since the pressure cannot further increase above a specific threshold when the positive displacement elements are removed.

A method and an apparatus for operating a peristaltic pump, in particular a peristaltic pump for conveying fluids in extracorporeal blood treatment apparatuses, are known from WO 2007/104435 A2. In order to monitor the correct operation of the peristaltic pump, the power consumption of the pump or a physical variable correlated to the power consumption is monitored. The monitoring of the pump current is based on the pump current having a periodically unchanging DC component on which a periodically changing AC component is superimposed.

U.S. Pat. No. 5,629,871 describes a method and an apparatus for monitoring the operability of individual modules of a haemodialysis apparatus. These also include the peristaltic pumps, the pump current or the supply voltage of the peristaltic pumps being monitored in order to be able to determine a failure of the pump.

An extracorporeal blood treatment apparatus is known from EP 2 918 837 A1, in which apparatus the removal of the resiliently mounted positive displacement elements is monitored by means of a force transducer in order to detect a blockage of the hose line.

The object of the invention is to reliably detect a blockage of the fluid flow in a hose line of a tube set of a medical treatment apparatus, in particular an extracorporeal blood treatment apparatus. Another object of the invention is to be able to monitor the correct operation of a peristaltic pump, in particular a peristaltic pump of an extracorporeal blood treatment apparatus. Another object of the invention is to provide a method which makes it possible to reliably detect a blockage of the fluid flow in a hose line of a tube set of a medical treatment apparatus and to monitor the correct operation of a peristaltic pump. Another object of the invention is to produce a tube set for a medical treatment apparatus that is easy to handle and which, in connection with a monitoring apparatus, allows monitoring of the blood treatment.

These objects are achieved according to the invention by means of the features of the independent claims. The dependent claims relate to advantageous embodiments of the invention.

The invention is based on the fact that the occlusion of the positive displacement elements of the peristaltic pumps for conveying the fluid in the hose line is monitored in order to monitor the fluid flow in a hose line. It is basically immaterial to the invention what fluid is conveyed by the peristaltic pump. However, the invention requires a particular conductivity of the fluid.

The basic principle of the invention consists in detecting a blockage of the fluid flow in the hose line not by monitoring components of the positive displacement pump itself, but by monitoring the electrical resistance or a variable of the fluid in a hose segment of the hose pipe which correlates with the electrical resistance. For this purpose, the electrical resistance or a variable of the fluid which correlates with the electrical resistance is measured between a first and a second electrode, the first electrode being arranged on the hose line upstream of the occlusion elements of the peristaltic pump and the second electrode being arranged on the hose line downstream of the occlusion elements such that an electrical contact is produced between the first and second electrode and the fluid flowing in the hose line. Consequently, it is not the position of the positive displacement elements that is detected, but rather the electrical resistance or the variable of the fluid which correlates with the electrical resistance.

The invention is based on the knowledge that the positive displacement elements squeeze the hose line during correct operation of the peristaltic pump, such that the electrical resistance, which depends on the fluid located in the hose segment, is high or the conductivity is low. If the positive displacement elements are removed when there is an overpressure in the hose line as a result of a blockage of the fluid flow, the electrical resistance decreases in the relevant hose line portion and the conductivity increases.

The medical treatment apparatus according to the invention comprises a tube set which can have one or more hose lines, and a peristaltic pump for conveying fluid, which comprises a receiving unit, comprising a pump bed for inserting a hose segment of the hose line, and movable occlusion elements for acting on the hose segments inserted into the pump bed, and a monitoring apparatus for monitoring the occlusion of the occlusion elements of the peristaltic pump. The peristaltic pump can be designed in different ways, as long as the pump has positive displacement elements.

The monitoring apparatus comprises a device for measuring the electrical resistance or a variable which correlates with the electrical resistance between a first and a second electrode. A variable which correlates with the electrical resistance can be the conductivity or the current or the voltage (Ohm's law). The first electrode is arranged on the hose line upstream of the occlusion elements and the second electrode is arranged on the hose line downstream of the occlusion elements such that an electrical contact can be produced between the first and second electrode and the fluid flowing in the hose line. In addition, the monitoring apparatus comprises a calculation and evaluation unit which detects the electrical resistance or the variable which correlates with the electrical resistance.

The calculation and evaluation unit can be designed in different ways in order to monitor the occlusion. All that matters is that the calculation and evaluation unit detects the occlusion as the result of a change in the electrical resistance or in a variable which correlates with the electrical resistance, for example by the predetermined lower and/or upper threshold value being exceeded or undershot, respectively.

A preferred embodiment provides for the calculation and evaluation unit to be designed such that a change in the electrical resistance is detected, a lack of occlusion of the occlusion elements being concluded if the electrical resistance falls below a predetermined threshold value, or such that a change in the electrical conductivity is detected, a lack of occlusion of the occlusion elements being concluded if the electrical conductivity exceeds a predetermined threshold value.

The advantages of the monitoring according to the invention can be seen in particular in a peristaltic pump, the receiving unit of which has an arcuate pump bed. In a roller pump of known design of this kind, the hose segment to be inserted into the pump forms a loop. The first electrode and the second electrode are preferably arranged in the region of the intersecting hose portions of the loop, to which the electrodes can be fixed adequately, and relatively close to one another, upstream and downstream of the occlusion elements.

A particularly preferred embodiment provides for the tube set to comprise a connecting piece or a fixing piece by means of which the intersecting portions of the hose segment forming a loop are fixed, the first and second electrodes being component parts of the connecting piece. Consequently, the electrodes are component parts of the connecting piece in that the electrodes are adequately fixed to the hose line at a relatively small distance from one another. The structural design and the handling process of the tube set are thus simplified. For example, all of the connecting lines can be guided out of the connecting piece in a single cable. In addition, the electrical connection can also be produced by inserting the connecting piece into a receiving piece, corresponding contacts being provided on the connecting piece and the receiving piece. However, it is also in principle possible to provide the electrodes at other points of the hose line upstream or downstream of the occlusion elements.

The connecting piece is preferably a plastics part in which a first channel comprising an inlet and an outlet, and a second channel comprising an inlet and an outlet are formed, the first and second channels preferably intersecting, and in that the electrodes are formed in the wall of the first and second channel. The plastics part is preferably a plastics part formed as a single piece.

In another particularly preferred embodiment, the plastics material of the plastics part consists of a conductive and a non-conductive component, the plastics material in the region of the first and second channel in which the first and second electrodes are formed being a conductive plastics material for forming the electrodes. This provides the advantage that the electrodes are integral component parts of the connecting piece, meaning that the handling process is particularly simple. The connecting piece, together with the electrodes, can be cost-effectively produced in large numbers.

Conductive polymers can be found in the prior art. Micro steel fibres, carbon fibres or finely distributed metal particles, for example, can be incorporated in a non-conductive plastics material.

The connecting piece comprising the two components can be simply and cost-effectively produced by means of the known two component injection moulding process (2K process) in only one working step and using only one mould.

Integrating one or more electrodes in a plastics part of a tube set comprising one or more hose lines has independent inventive significance. The electrode can be used for various purposes.

The tube set for a medical treatment apparatus according to the invention is characterised in that the at least one electrode is a component part of a plastics part that consists of a conductive and a non-conductive component, in which plastics part at least one channel is formed which has an inlet, at which a hose segment of the hose line is connected, and has an outlet, at which a hose segment of the hose line is connected, the plastics material in a region of the plastics part in which the electrode is formed being a conductive plastics material. The plastics part can be provided at any point of the hose line. The adjacent hose line portions can be connected at the inlet or outlet, respectively, of the connecting piece. These portions can be adhesively bonded or welded to the plastics part, for example.

An embodiment of the invention is explained in more detail below with reference to the drawings, in which.

Figure 1:
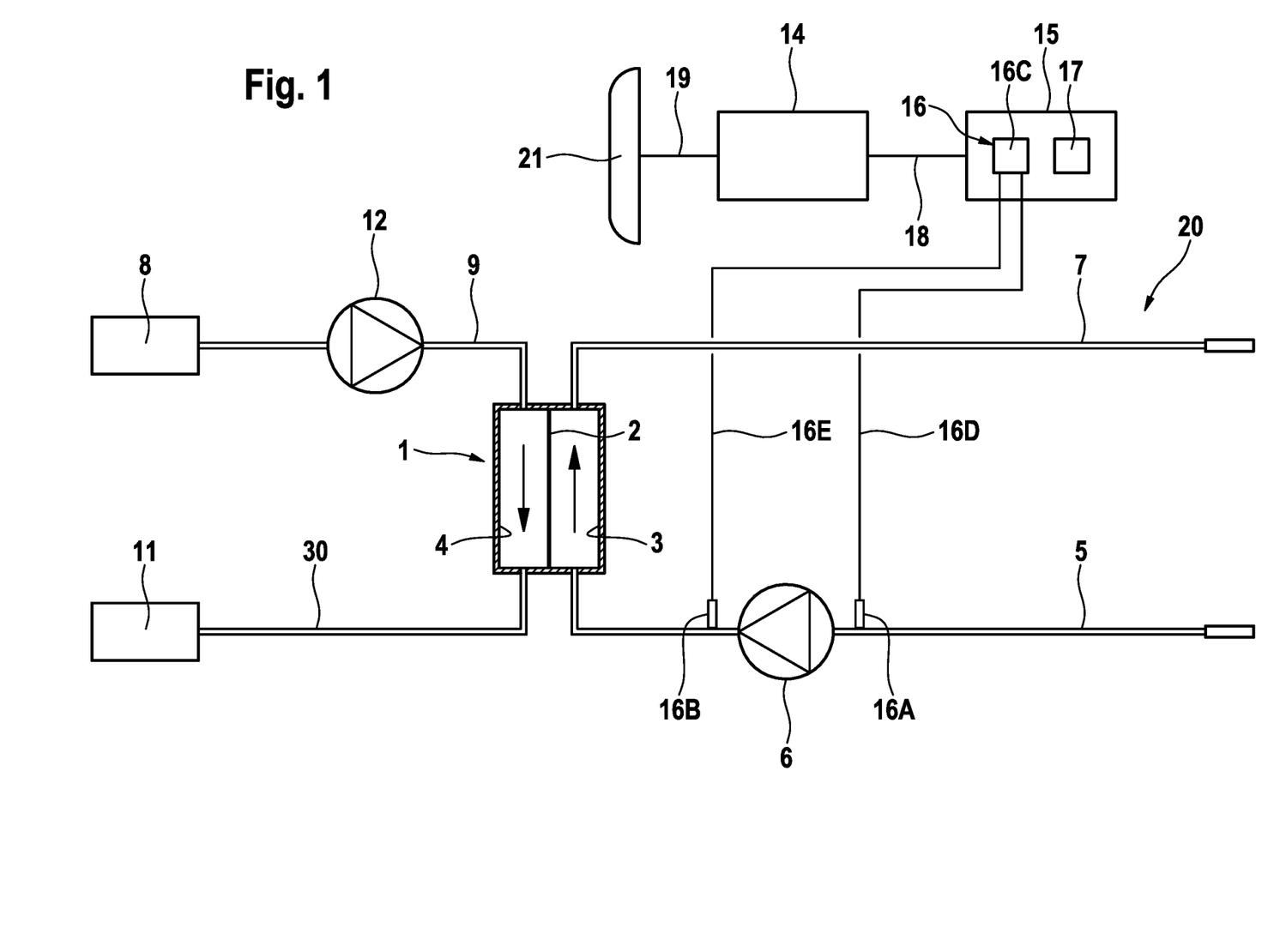
FIG. 1 is a simplified schematic view of a medical treatment apparatus according to the invention which comprises a monitoring apparatus for monitoring the occlusion of the peristaltic pump.

In the present embodiment, the medical treatment apparatus is an extracorporeal blood treatment apparatus, in particular a haemodialysis apparatus, which has a dialyser 1 which is divided into a blood chamber 3 and a dialysate chamber 4 by a semi-permeable membrane 2. An arterial blood line 5, in which a blood pump 6 is arranged, leads from a patient to an inlet of the blood chamber 3, whilst a venous blood line 7 leads from an outlet of the blood chamber to the patient.

The fresh dialysate is provided in a dialysate source 8. A dialysate supply line 9 leads from the dialysate source 8 to an inlet of the dialysate chamber 4 of the dialyser 1, whilst a dialysate discharge line 30 leads from an outlet of the dialysate chamber 4 to a drain 11. A dialysate pump 12 is arranged in the dialysate discharge line 30.

The blood pump 6 is a peristaltic pump, in particular a roller pump, the arterial and venous blood lines 5, 7, being flexible hose lines of a tube set 20 intended for single use (disposable).

Figure 2:
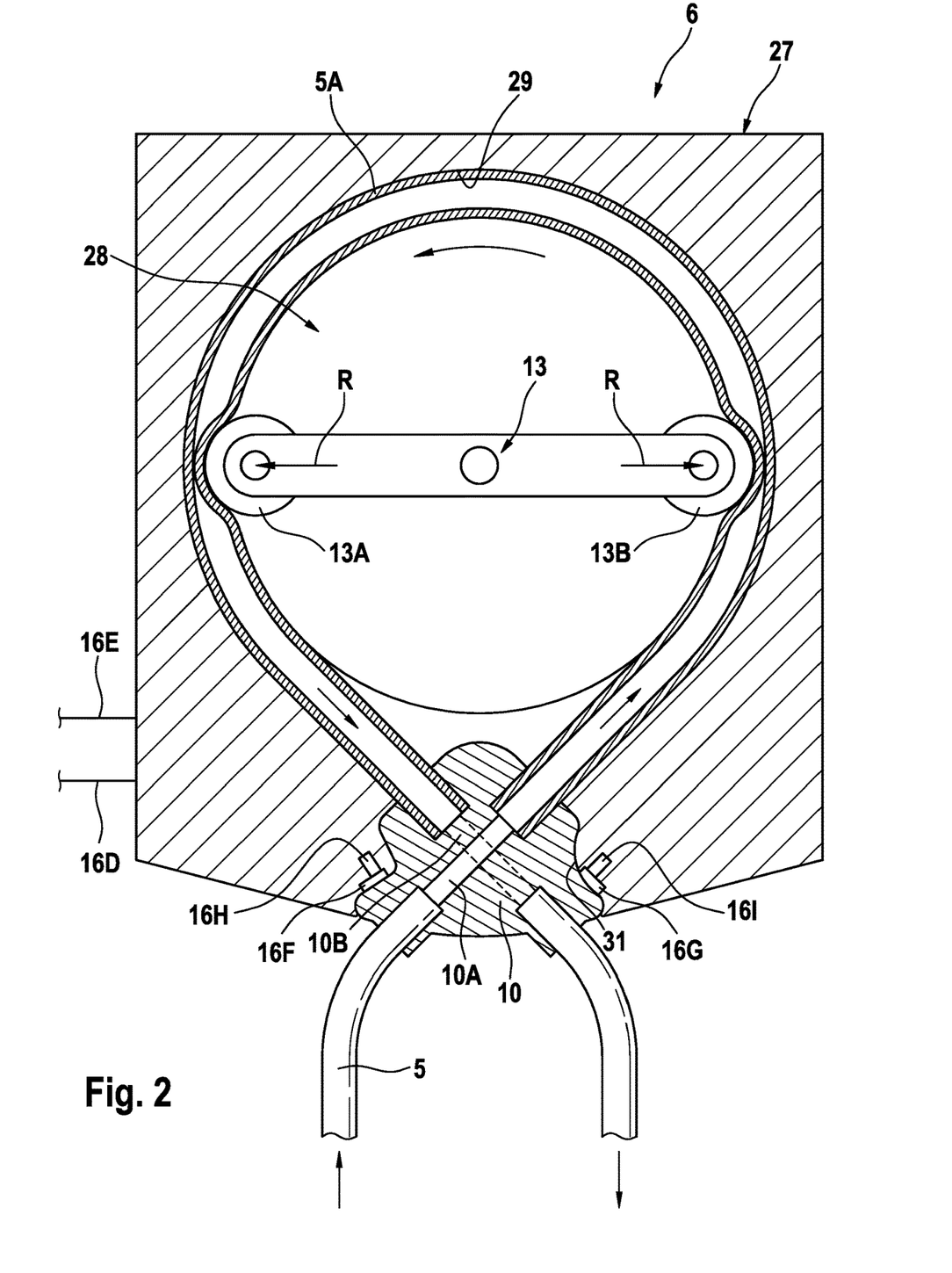
FIG. 2 is a simplified schematic view of the peristaltic pump of the medical treatment apparatus.

FIG. 2 is a simplified schematic view of the peristaltic pump 6. The peristaltic pump 6 comprises a housing body 27 having a receiving unit 28, into which a hose segment 5A of the arterial hose line 5 is inserted. The hose segment forms a loop which is fitted in an arcuate pump bed 29 formed in the receiving unit 28. The intersecting portions of the hose line 5 are fixed by a connecting piece 10 which is fitted, preferably in a latching manner, into a recess 31 in the housing body 27. A peristaltic pump of this kind is known from WO 2005/111424 A1.

Figure 3:
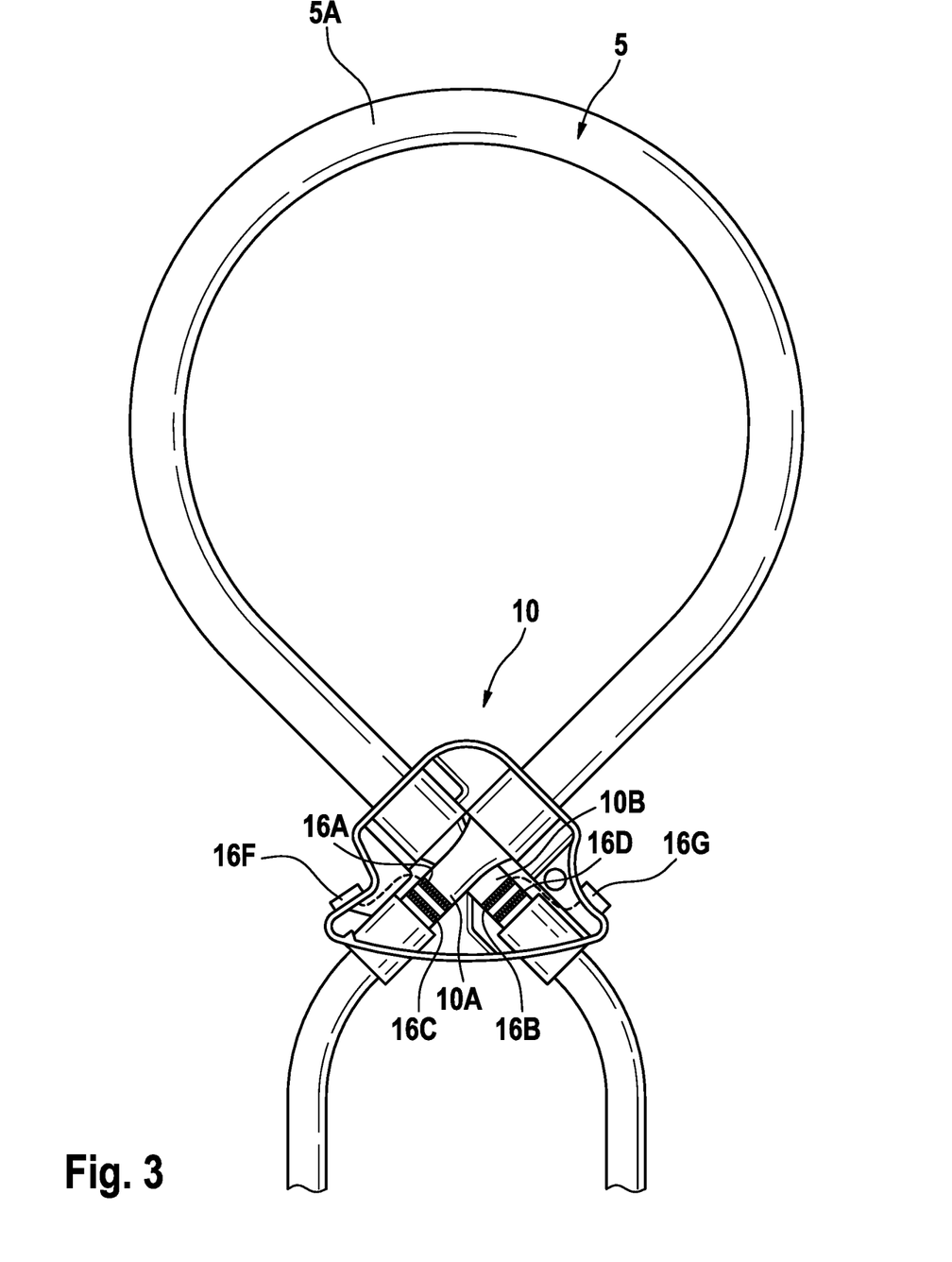
FIG. 3 is a simplified schematic view of the hose segment to be inserted into the peristaltic pump, together with a connecting piece and the adjacent hose line portions.

In the present embodiment, the peristaltic pump comprises rollers 13A, 13B as positive displacement elements, which rollers are rotatably mounted on a rotor 13 which is enclosed by the pump bed 29. The rollers are resiliently pre-loaded on the rotor 13 against the hose line 5 in the radial direction R. During correct operation, the rollers 13A, 13B completely squeeze the hose line 5, as shown in FIG. 3. Since the rollers 13A, 13B are resiliently pre-loaded on the rotor 13, the rollers can be removed from the hose line 5 if the pressure increases as a result of a blockage of the fluid flow in the hose line 5 downstream of the pump 6. The roller pump can also have more than two rollers.

The blood treatment apparatus comprises a central control and calculating unit 14 and can have additional components, for example a balancing device or an ultrafiltration device, and various sensors for monitoring the blood treatment, which are not, however, shown in FIG. 1.

In addition, the blood treatment apparatus comprises a monitoring apparatus 15 for monitoring the occlusion of the positive displacement elements 13A, 13B of the peristaltic pump. The monitoring apparatus 15 comprises a device 16 for measuring the electrical resistance or a variable which correlates with the electrical resistance, and a calculation and evaluation unit 17, which can also be component parts of the central control and calculating unit 14 of the blood treatment apparatus.

The device 16 for measuring the electrical resistance comprises a first and a second electrode 16A, 16B, between which the electrical resistance is measured by means of a resistance or conductivity meter 16C. The first electrode 16A is connected to the resistance or conductivity meter 16C via a first electrical connecting line 16D, and the second electrode 16B is connected to the resistance or conductivity meter via a second electrical connecting line 16E. The two electrodes 16A, 16B are integral component parts of the connecting piece 10 of the hose line 5.

Figure 4:
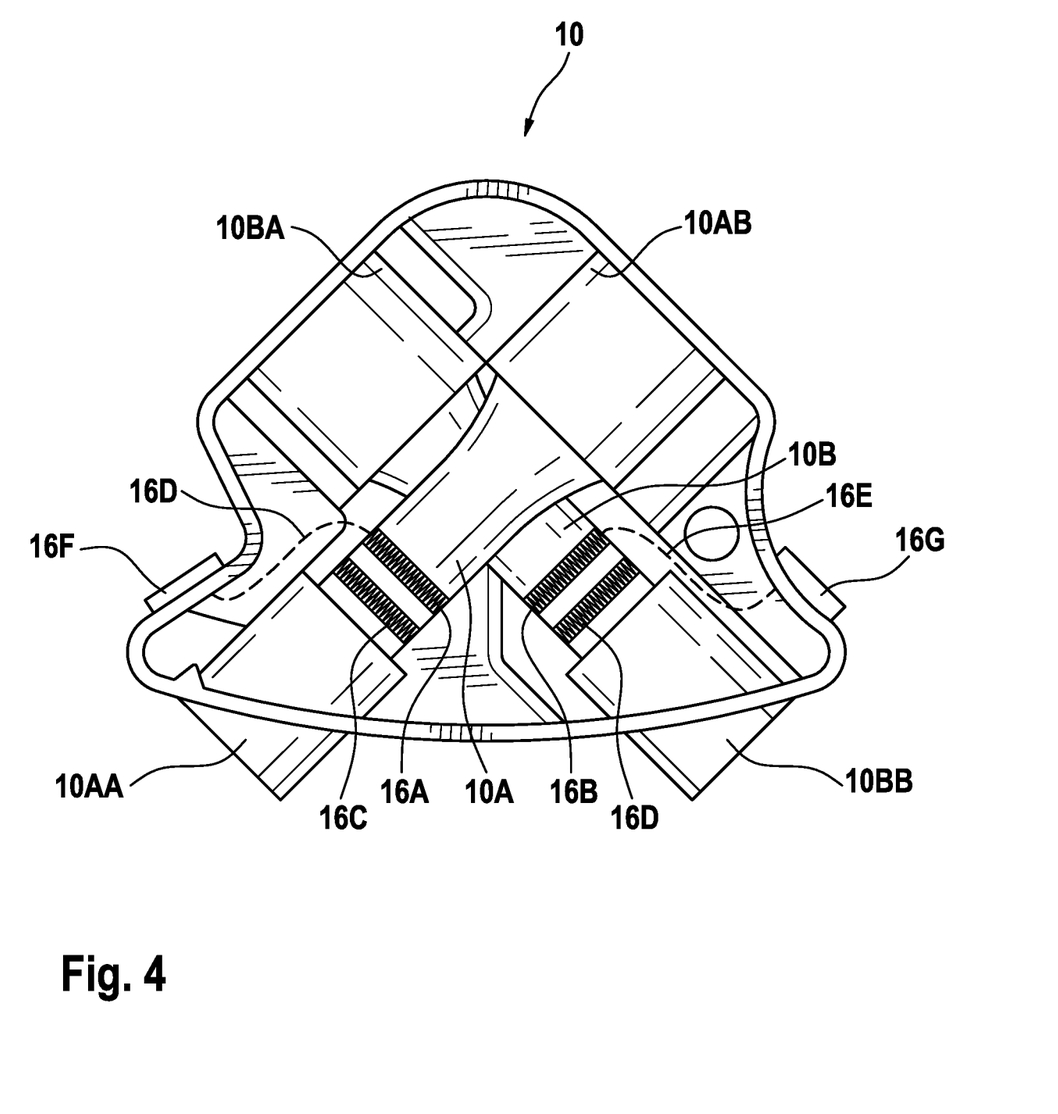
FIG. 4 is an enlarged view of the connecting piece.

FIGS. 3 and 4 show an embodiment of the connecting piece 10 shown schematically in FIG. 1, in which connecting piece the electrodes 16A, 16B are integrated. FIG. 4 is an enlarged view of the connecting piece 10. The connecting piece 10 is a plastics part which is preferably formed as a single piece, but which can also be formed as a plurality of pieces, for example consisting of a housing lower part and a housing upper part.

A first channel 10A and a second channel 10B are formed in the plastics part, which channels intersect. The end pieces of the first channel 10A are formed as an inlet piece and an outlet piece 10AA, 10AB and the end pieces of the second channel 10B are formed as an inlet piece and an outlet piece 10BA, 10BB. The adjacent hose line portions are connected to the inlet piece and the outlet piece 10AA, 10AB and 10BA, 10BB of the first and second channel 10A, 10B, such that the patient's blood flows through one channel 10A to the peristaltic pump 6 and through the other channel 10B from the pump.

The first electrode 16A is provided on the first channel 10A and the second electrode 16B is provided on the second channel 10B. The electrodes 16A, 16B are preferably annular electrodes which are formed in the wall of the channel, such that an electrical contact is produced between the electrode and the blood. The annular electrodes preferably extend over the entire cross section of the channel.

The plastics part 10 consists of a first component made of a non-conductive plastics material, and a second component made of a conductive plastics material, the annular electrodes 16A, 16B being made of the conductive plastics material. The conductive plastics material is shown by black shading in FIGS. 3 and 4. The connecting piece 10 is produced in the two component injection moulding process (2K injection moulding process), a conductive hemocompatible plastics material being used in the region of the channel 10A, 10B, in which the electrode 16A, 16B is intended to be formed. The annular electrodes are preferably formed as an annular extension of the hose line. The conductive plastics material can be, for example, a polymer compound made of polypropene and stainless steel fibres.

Additional electrodes 16C and 16D can also be integrated in the connecting piece 10, for example electrodes for leakage currents (earthing) or for coupling or decoupling additional signals.

Portions of the electrical connecting lines 16D, 16E for the electrodes 16A, 16B are also formed in the connecting piece 10 as tracks made of a conductive plastics material. The ends of these conductive tracks are formed as connection contacts 16F, 16G, which come into contact with corresponding connection contacts 16H, 16I on the receiving unit 28 when the connecting piece 10 is inserted into the recess 31 in the receiving unit 28 of the housing body 27. As a result, the electrical connection to the resistance or conductivity meter 16C can be produced in a particularly simple manner, and therefore the handling process is further simplified.

The calculation and evaluation unit 17 can be designed in different ways. For example, the calculation and evaluation unit 17 can be a microcomputer, on which a data processing program (software) runs. The calculation and evaluation unit 17 is designed such that the resistance measured between the electrodes 16A, 16B is compared with a predetermined threshold value. The measurement takes place at a high resistance. As long as the positive displacement elements 13A, 13B are not removed from the hose line 5, the measured resistance is high. If the resistance falls below a threshold value, it is concluded that the positive displacement elements 13A, 13B have been removed from the hose line 5. Instead of the resistance, the conductivity can also be measured. As long as the positive displacement elements 13A, 13B are not removed from the hose line 5, the conductivity measured is low. If the conductivity increases above the threshold value, it is concluded that the positive displacement elements have been removed from the hose line. The magnitude of the resistance or the conductivity is also a measurement for the distance by which the positive displacement elements 13A, 13B have been removed, since the cross section for conductive fluid, in particular blood, to pass through increases when the positive displacement elements 13A, 13B are pushed back against the resilient force. Consequently, by evaluating the resistance or the conductivity, the position of the positive displacement elements can also be concluded, it being possible to calculate or empirically determine the dependency of the position of the positive displacement elements on the resistance or the conductivity from the relevant flow cross sections, taking account of the resistance or the conductivity of the fluid. A corresponding function or the corresponding value can be stored in a memory of the calculation and evaluation unit 17, and therefore the calculation and evaluation unit 17 can calculate the position of the positive displacement elements.

The central control and calculating unit 14 is connected to the monitoring apparatus 15 via a data line 18. If the monitoring apparatus 15 detects a removal of the positive displacement elements 13A, 13B by a particular amount as a result of an increase in pressure in the hose line, the monitoring apparatus 15 generates a control or alarm signal, which is received by the central calculation and control unit 14. The central calculation and control unit 14 is connected via a data line 19 to an alarm unit 21, which emits an alarm. The central calculation and control unit 14 can also intervene in the machine control, for example stopping the peristaltic pump.

The monitoring apparatus 15 can also generate a control signal (data signal), which is dependent on the displacement of the positive displacement elements 13A, 13B. This signal can be received by a display unit (not shown), on which the position of the positive displacement elements is displayed.

The invention claimed is:

1. A medical treatment apparatus comprising:
   a tube set that comprises one or more hose lines,
   a peristaltic pump for conveying fluid, which comprises a receiving unit having a pump bed for inserting a hose segment of a hose line of the one or more hose lines, and movable occlusion elements for acting on the hose segment inserted into the pump bed, the movable occlusion elements resiliently pre-loaded against the hose segment in a radial direction, and
   a monitoring apparatus for monitoring the occlusion of the movable occlusion elements of the peristaltic pump by determining whether the movable occlusion elements are pushed back against the resiliently pre-loaded force,
   wherein the monitoring apparatus comprises:
   a device for measuring electrical resistance or a variable which correlates with the electrical resistance between a first and a second electrode, the first electrode being arranged on the hose line upstream of the movable occlusion elements and the second electrode being arranged on the hose line downstream of the movable occlusion elements of the peristaltic pump such that an electrical contact can be produced between the first and second electrode and the fluid flowing in the hose line, and
   a calculation and evaluation unit that detects the electrical resistance or a variable that correlates with the electrical resistance.

2. The medical treatment apparatus according to claim 1, wherein the calculation and evaluation unit is designed such that a change in the electrical resistance is detected, a lack of occlusion of the movable occlusion elements being concluded if the electrical resistance falls below a predetermined threshold value, or
   such that a change in the electrical conductivity is detected, a lack of occlusion of the movable occlusion elements being concluded if the electrical conductivity exceeds a predetermined threshold value.

3. The medical treatment apparatus according to claim 1, wherein the receiving unit of the peristaltic pump comprises an arcuate pump bed, the hose segment to be inserted into the receiving unit forming a loop.

4. The medical treatment apparatus according to claim 3, wherein the first electrode and the second electrode are arranged in the region of intersecting portions of the hose segment that forms the loop.

5. The medical treatment apparatus according to claim 3, wherein the tube set comprises a connecting piece, by means of which intersecting portions of the hose segment forming the loop are fixed, and the first electrode and the second electrode are component parts of the connecting piece.

6. The medical treatment apparatus according to claim 5, wherein the connecting piece is a plastics part comprising a wall, a first channel comprising an inlet and an outlet and a second channel comprising an inlet and an outlet are formed in the connecting piece, and the first electrode and the second electrode are formed in the wall.

7. The medical treatment apparatus according to claim 6, wherein the plastics material of the connecting piece consists of a conductive and a non-conductive component, and the plastics material in the region of the first channel and the second channel in which the first and second electrodes are formed comprises a conductive plastics material for forming the electrodes.

8. The medical treatment apparatus according to claim 1, wherein the first and/or second electrodes are annular electrodes.

9. The medical treatment apparatus according to claim 1, wherein the medical treatment apparatus is a blood treatment apparatus comprising an extracorporeal blood circuit, the tube set being a blood tube set and the hose segment being a blood line that is inserted into the receiving unit of the peristaltic pump.

10. A tube set for a medical treatment apparatus, comprising one or more hose lines, and at least one electrode provided on a hose line of the one or more hose lines for connecting at least one electrical line of a monitoring apparatus, wherein the at least one electrode is a component part of a connecting piece made of a plastics material consisting of a conductive and a non-conductive component, at least one channel is formed in the connecting piece, the at least one channel comprises an inlet to which a hose segment of the one or more hose lines is connected and an outlet to which a hose segment of the one or more hose lines is connected, the plastics material in a region in which the electrode is formed comprises a conductive plastics material, the connecting piece is configured to fit within a recess of a housing body of a peristaltic pump, and the connecting piece further comprises at least one connection contact electrically connected to the at least one electrode, the at least one connection contact configured to come into contact with a corresponding connecting contact of the housing body when the connecting piece is within the recess.

11. The tube set according to claim 10, wherein the at least one electrode is a first and a second electrode that are provided on the hose segment of the hose line for connecting a first and a second electrical line of a monitoring apparatus configured to monitor occlusion of movable occlusion elements of the peristaltic pump.

12. The tube set according to claim 10, wherein the hose segment of the hose line, at which the first and second electrodes are provided, forms a loop for inserting into an arcuate pump bed of a receiving unit of the peristaltic pump, and intersecting portions of the hose segments are fixed to the connecting piece.

13. The tube set according to claim 12, wherein the at least one channel comprises a first channel and a second channel, the first channel comprises an inlet and an outlet, the second channel comprises an inlet and an outlet, the first channel and the second channel are formed in the connecting piece, and the electrodes are formed in the wall of the first and second channels.

14. The tube set according to claim 10, wherein the at least one electrode is an annular electrode.

15. A method for monitoring the occlusion of movable occlusion elements of a peristaltic pump for conveying a fluid for a medical treatment apparatus, the peristaltic pump comprising a receiving unit having a pump bed for inserting a hose segment of a hose line, and the movable occlusion elements for acting on the hose segment inserted into the pump bed, wherein electrical resistance or a variable that correlates with the electrical resistance is measured between a first and a second electrode, the first electrode being arranged on the hose line upstream of the movable occlusion elements and the second electrode being arranged on the hose line downstream of the movable occlusion elements such that an electrical contact is produced between the first and second electrode and fluid flowing in the hose line, the electrical resistance or the variable that correlates with the electrical resistance is detected, and, if a change in the electrical resistance is detected, a lack of occlusion of the movable occlusion elements is concluded if the electrical resistance falls below a predetermined threshold value or if the electrical conductivity exceeds a predetermined threshold value.

\* \* \* \* \*